(12) United States Patent  
Fessler

(10) Patent No.: US 11,103,289 B2  
(45) Date of Patent: Aug. 31, 2021

(54) INTERSPINOUS PROCESS FUSION DEVICE AND METHOD OF USE

(71) Applicant: IN QUEUE INNOVATIONS, LLC, Winona Lake, IN (US)

(72) Inventor: Richard G. Fessler, Winnetka, IL (US)

(73) Assignee: IN QUEUE INNOVATIONS, LLC, Winona Lake, IN (US)

( * ) Notice: Subject to any disclaimer, the term of this patent is extended or adjusted under 35 U.S.C. 154(b) by 67 days.

(21) Appl. No.: 16/214,894

(22) Filed: Dec. 10, 2018

(65) Prior Publication Data

US 2019/0105084 A1 Apr. 11, 2019

Related U.S. Application Data

(63) Continuation of application No. 15/211,600, filed on Jul. 15, 2016, now Pat. No. 10,154,860, which is a continuation of application No. 14/349,118, filed as application No. PCT/US2012/058478 on Oct. 2, 2012, now Pat. No. 9,393,053.

(Continued)

(51) Int. Cl.
   *A61B 17/70* (2006.01)
   *A61B 17/00* (2006.01)

(52) U.S. Cl.
   CPC ...... *A61B 17/7065* (2013.01); *A61B 17/7071* (2013.01); *A61B 17/7067* (2013.01); *A61B 2017/00858* (2013.01)

(58) Field of Classification Search
   CPC ............ A61B 17/7062; A61B 17/7065; A61B 17/7067; A61B 17/56; A61B 17/88; A61B 2017/564

See application file for complete search history.

(56) References Cited

U.S. PATENT DOCUMENTS 5,390,683 A  2/1995  Pisharodi  
5,658,335 A  8/1997  Allen  
(Continued)

OTHER PUBLICATIONS

International Search Report and Written Opinion of the International Searching Authority for PCT/US2012/058478, dated Mar. 25, 2013, 10 pages.

(Continued)

*Primary Examiner* — Ellen C Hammond  
(74) *Attorney, Agent, or Firm* — Heslin Rothenberg Farley & Mesiti P.C.; Jacquelyn A. Graff, Esq.

(57) ABSTRACT

The present invention discloses an interspinous process fusion device, a method of fabricating the interspinous process fusion device, and a surgical method for maintaining a space between two spinous processes in a spine of a patient using the fusion device. The interspinous process fusion device including a distal tip member, a middle plate, a proximal plate, an elongate member, and a plurality of movable wings. The elongate member having a first end, a second end, and a longitudinal axis extending between the first and second end. The distal tip member is connected to the first end of the elongate member, the proximal plate is connected to the second end of the elongate member, and the middle plate and plurality of wings are positioned intermediate the distal tip member and the proximal plate along the longitudinal axis to form the interspinous process fusion device assembly.

19 Claims, 13 Drawing Sheets

Related U.S. Application Data

(60) Provisional application No. 61/542,512, filed on Oct. 3, 2011.

(56) References Cited

U.S. PATENT DOCUMENTS

| | | | |
|---|---|---|---|
| 8,105,358 B2 | 1/2012 | Phan | |
| 9,084,640 B2 | 7/2015 | Dwyer et al. | |
| 2003/0083688 A1* | 5/2003 | Simonson | A61B 1/32 606/191 |
| 2007/0032790 A1 | 2/2007 | Aschmann et al. | |
| 2008/0108990 A1 | 5/2008 | Mitchell et al. | |
| 2009/0198337 A1 | 8/2009 | Phan | |
| 2009/0234389 A1* | 9/2009 | Chuang | A61B 17/7065 606/249 |
| 2009/0265006 A1* | 10/2009 | Seifert | A61B 17/7062 623/17.16 |
| 2009/0292316 A1* | 11/2009 | Hess | A61B 17/7065 606/249 |
| 2010/0234889 A1 | 9/2010 | Hess | |
| 2010/0318127 A1 | 12/2010 | Phan et al. | |
| 2011/0190816 A1 | 8/2011 | Sheffer et al. | |

OTHER PUBLICATIONS

International Preliminary Report on Patentability for PCT/US2012/058478 and Written Opinion of the International Searching Authority, dated Apr. 8, 2014, 6 pages.
Extended European Search Report for European Application No. 12839130.7, dated Nov. 19, 2015, 8 pages.
Patent Examination Report for Australian Patent Application No. 2012318811, dated Apr. 26, 2016, 3 pages.
Extended European Search Report for European Application No. 17167817.0, dated Oct. 2, 2017, 9 pages.

* cited by examiner

INTERSPINOUS PROCESS FUSION DEVICE AND METHOD OF USE

CROSS-REFERENCE TO RELATED APPLICATION

This application is a continuation application of U.S. patent application Ser. No. 15/211,600, filed Jul. 15, 2016, which is a continuation application of U.S. patent application Ser. No. 14/349,118, filed Apr. 2, 2014 (U.S. Pat. No. 9,393,053), which is a national stage filing under section 371 of International Application No. PCT/US2012/058478 filed on Oct. 2, 2012, and published in English on Apr. 11, 2013 as WO 2013/052496 A2 and claims priority benefit under 35 U.S.C. § 119(e) of U.S. Provisional Patent Application No. 61/542,512 filed Oct. 3, 2011, which are each incorporated herein by reference in their entireties.

TECHNICAL FIELD

The present invention relates generally to general surgery, orthopaedic and neurosurgical implants used for insertion within a space between hard tissue structures, and more specifically, but not exclusively, concerns devices implanted between interspinous processes to maintain or reestablish proper spacing within the spine.

BACKGROUND OF THE INVENTION

Fusion of the lumbar and thoracic spine currently involves either fixation posteriorly using pedicle screws or anteriorly using plates or rods applied directly to the vertebral bodies. Often these require major open exposures and extensive dissections of soft tissues. Recently, instrumentation and implants have been developed which enable both fusion and fixation to be performed through minimally invasive techniques, however, fixation with pedicle screws or anterior plates when performed with minimally invasive (MIS) techniques requires significant technical skill. Surgical errors and/or procedures performed with less than advanced surgical technique often results in patient morbidity.

Interspinous process fusion techniques have also been developed. However, these surgical techniques also require moderate to significant soft tissue dissection and there are not true corresponding MIS interspinous process implants.

SUMMARY OF THE INVENTION

Advancement of the state of interspinous process implants and the related MIS surgical technique are believed desirable. The disclosed embodiment is designed to enable interspinous process fixation using MIS techniques. In doing so, it will eliminate the technical difficulties inherent to MIS instrumentation with pedicle screws, as well as the soft tissue dissection experienced with ALIF or open interspinous process fixation.

The present invention provides in one aspect, an interspinous process fusion device that has a distal tip, a middle plate, a proximal plate, an elongate member having a first end and a second end and a longitudinal axis that extends between the first end and the second end, and a plurality of movable wings. The distal tip member is connected to the first end of the elongate member and the proximal plate is connected to the second end of the elongate member with the middle plate and plurality of wings being positioned intermediate the distal tip member and the proximal plate along the longitudinal axis.

The present invention provides in another aspect a method of fabricating an interspinous process fusion device, the method may include the steps of obtaining an elongate member having a first end and a second end. The method may also have the step of obtaining a distal tip member, a middle plate, a proximal plate, a first pair of wings, and a second pair of wings. A further step may be connecting the proximal plate to the second end. An additional step may also be inserting two actuation screws through corresponding openings in each of the first pair of wings, the two actuation screws being detachably connected to the proximal plate. The method may also include the steps of inserting the elongate member and the two actuation screws through a plurality of openings in the middle plate to position the middle plate adjacent to the first pair of wings and inserting the two actuation screws through corresponding openings in each of the second pair of wings. The method may further include the step of connecting the distal tip member to the first end of the elongate member to form the fusion device The present invention provides in another aspect, a surgical method for maintaining a space between two interspinous processes, the method may include the step of obtaining a medical device that has a distal tip member, a middle plate, a proximal plate, an elongate member having a first end and a second end and a longitudinal axis extending between the first end and the second end, and a plurality of movable wings. The method may also include the step of inserting the medical device thorough an opening in the skin of the patient. A further step of the method may be positioning the medical device between a top spinous process and a bottom spinous process. The method may also include the step of moving the plurality of wings to pressingly engage the top spinous process and the bottom spinous process to maintain the space between the top and bottom spinous processes.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features and advantages of the invention are apparent from the following detailed description taken in conjunction with the accompanying drawings in which:

DETAILED DESCRIPTION FOR CARRYING OUT THE INVENTION

Generally stated, disclosed herein is an interspinous process fusion device that typically includes a distal tip, a middle plate, a proximal plate, four fins or wings and three securement screws. As used herein, the terms "interspinous process fusion device", "device", "fusion device", "implant" and "fusion implant" may be used interchangeable as they essentially describe the same type of device. Further, a method of assembling the device is discussed. Finally, also described herein is a surgical method for using the interspinous process fusion device to maintain a space between two vertebral bodies within a patient suffering from a diseased or damaged spinal column.

In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of an implant nearest the torso, while "distal" indicates the portion of the implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. In addition, for the purposes of this disclosure when referencing the device, the term "proximal" will mean the portion of the device closest or nearest the insertion instrument. The term "distal" shall mean the portion of the device farthest away from the insertion instrument.

Figure 1:
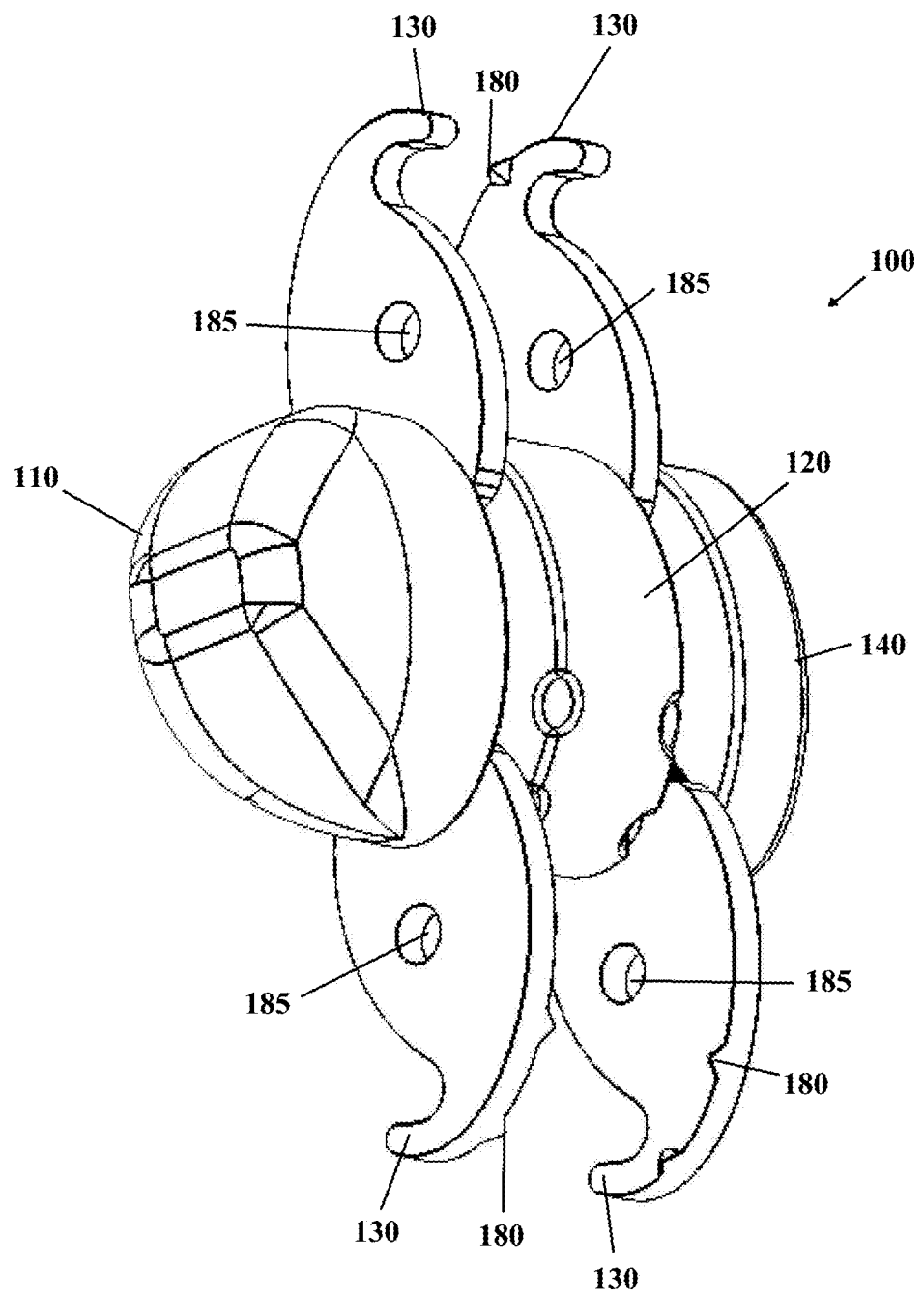
FIG. 1 is a posterior, distal perspective view of one embodiment of an interspinous process fusion device, in accordance with an aspect of the present invention.
Figure 2:
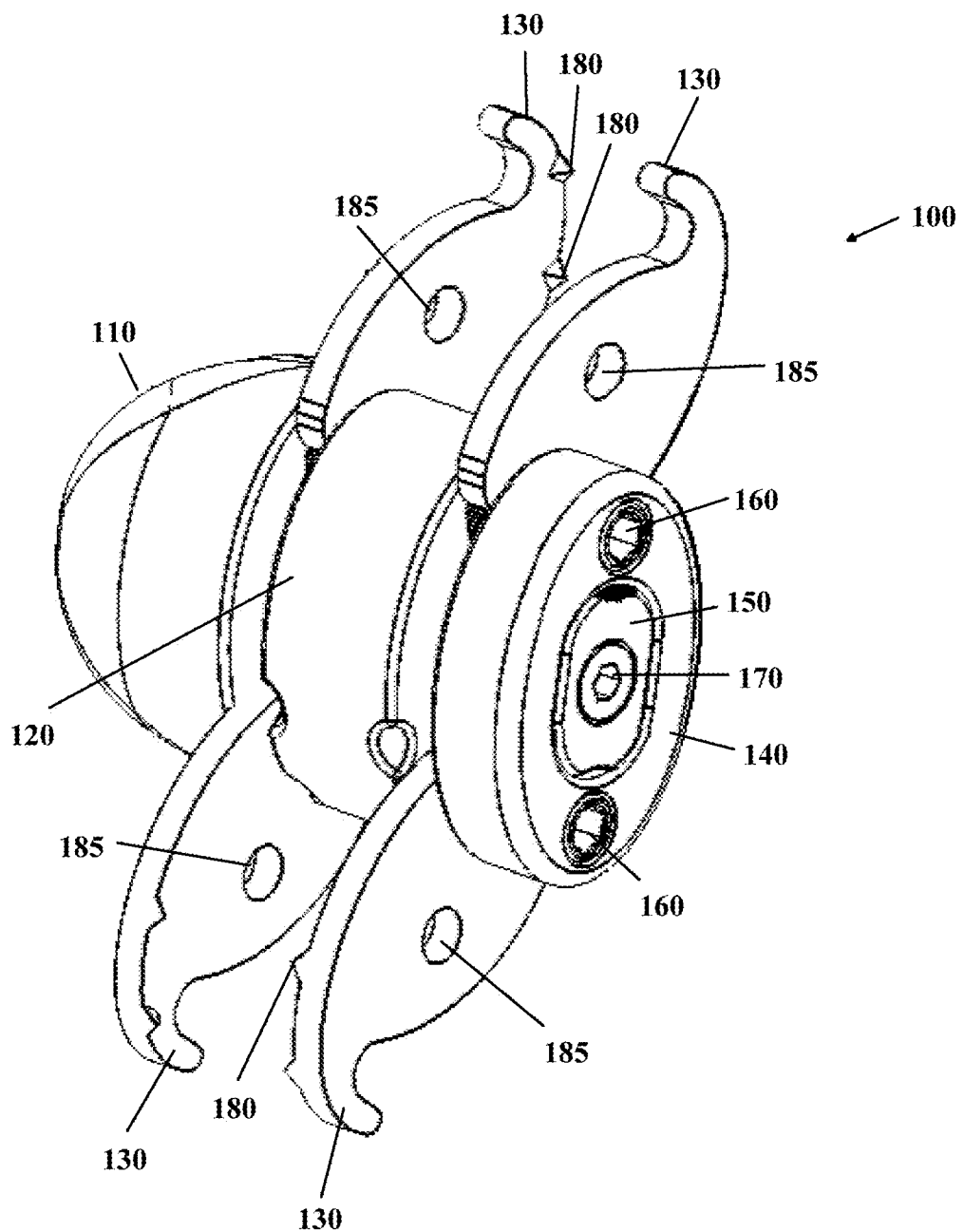
FIG. 2 is a posterior, lateral perspective view of the interspinous process fusion device of FIG. 1, in accordance with an aspect of the present invention.
Figure 3:
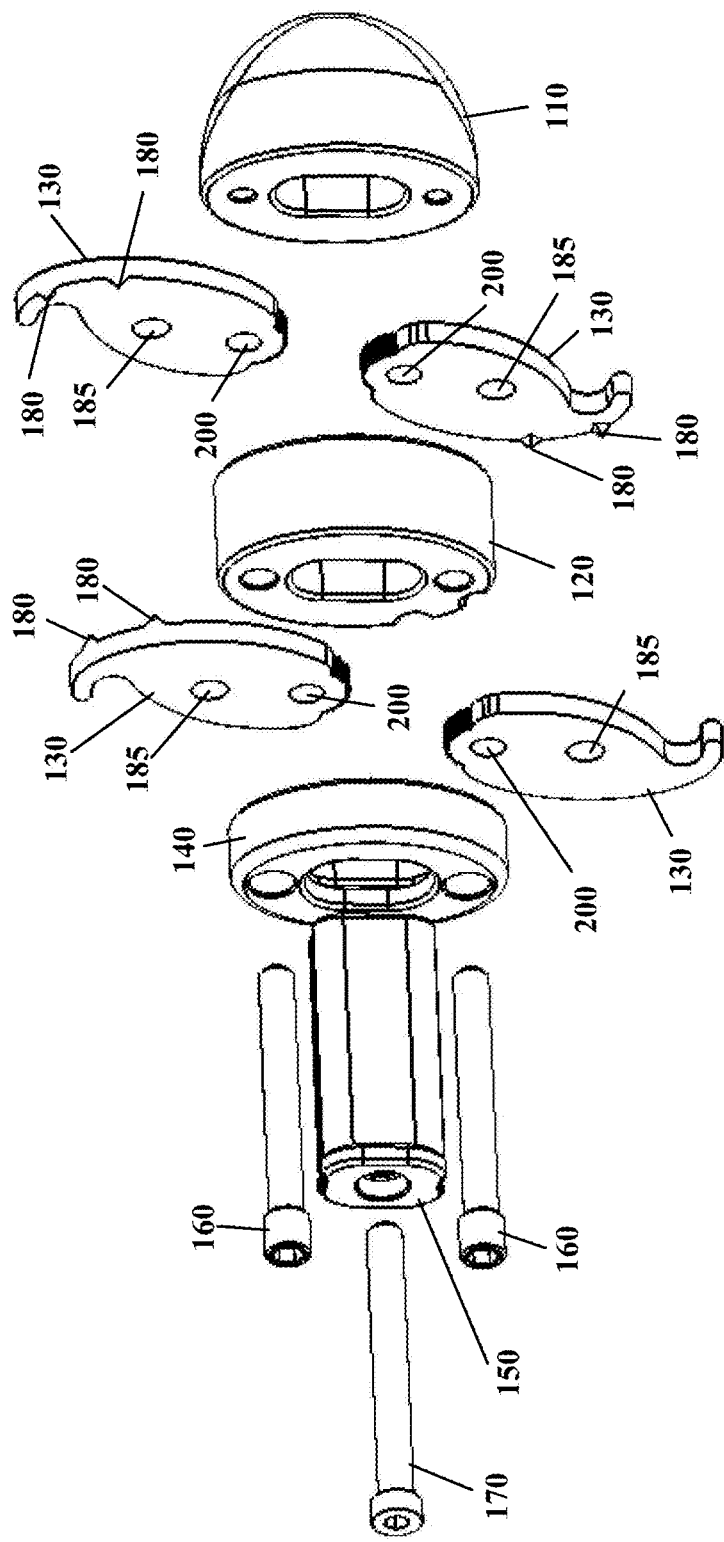
FIG. 3 is an exploded view of the interspinous process fusion device of FIG. 1, in accordance with an aspect of the present invention.

Referring now to FIG. 1, an example of the interspinous process fusion device 100 is shown. The device 100 as seen in FIGS. 1, 2 and 3 has a generally cylindrical geometry with a substantially straight external profile and bulbous or bullet shaped end to facilitate insertion between two spinous processes. The implant 100 may likely include a distal tip member 110, a middle plate 120, a plurality of fins or wings 130 and a proximal plate 140.

As seen in FIG. 2, for example purposes the device 100 includes in addition to the above noted elements, a locking insert 150, an inner locking screw or central bolt 170 and superior and inferior actuation screws 160. FIGS. 1 and 2 also show a means for fixation 180 disposed on the inner surface of wings 130. The means of fixation 180 may include but not be limited to spikes, pins, teeth and a roughed/textured/irregular/grid surface. The means for fixation 180 facilitates the capture and securement of the spinous processes between the wings when they are expanded.

Figure 8:
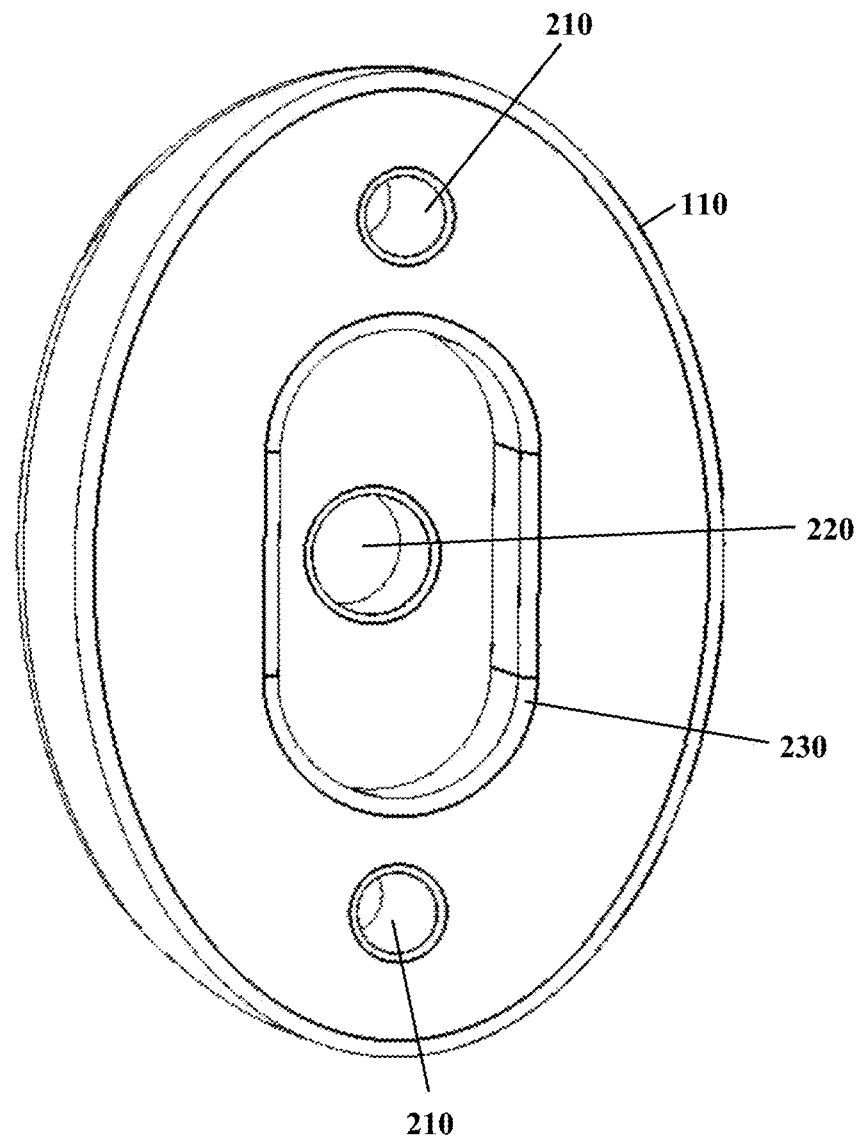
FIG. 8 is a medial view of the inner aspect of the distal tip of the interspinous process fusion device of FIG. 1, in accordance with an aspect of the present invention.

As depicted in the exploded view of FIG. 3, the device 100 includes distal tip member 110, a middle plate 120, a plurality of fins or wings 130 and a proximal plate 140 with a locking insert 150, an inner locking screw 170 and superior and inferior actuation screws 160. Briefly, the distal tip member 110 includes a generally bullet or convex shaped end with a planar surface at the opposite end of the member. The convex end is shaped to facilitate insertion into the body during the operative procedure as well as between the two adjacent spinous processes. The planar end is configured to facilitate the actuation of the two adjacent wings 130 when the device 100 is assembled. As seen in FIG. 8, the planar end may include, for example purposes, two outer holes 210 into which the superior and inferior actuation screws may be threaded to actuate and secure the positioning of the wings. The central hole 220 is sized to receive the inner locking screw following assembly of the device 100. The central depression 230 is configured to receive the locking insert after the locking insert has been positioned through the central aspect of the assembled device 100.

Figure 9:
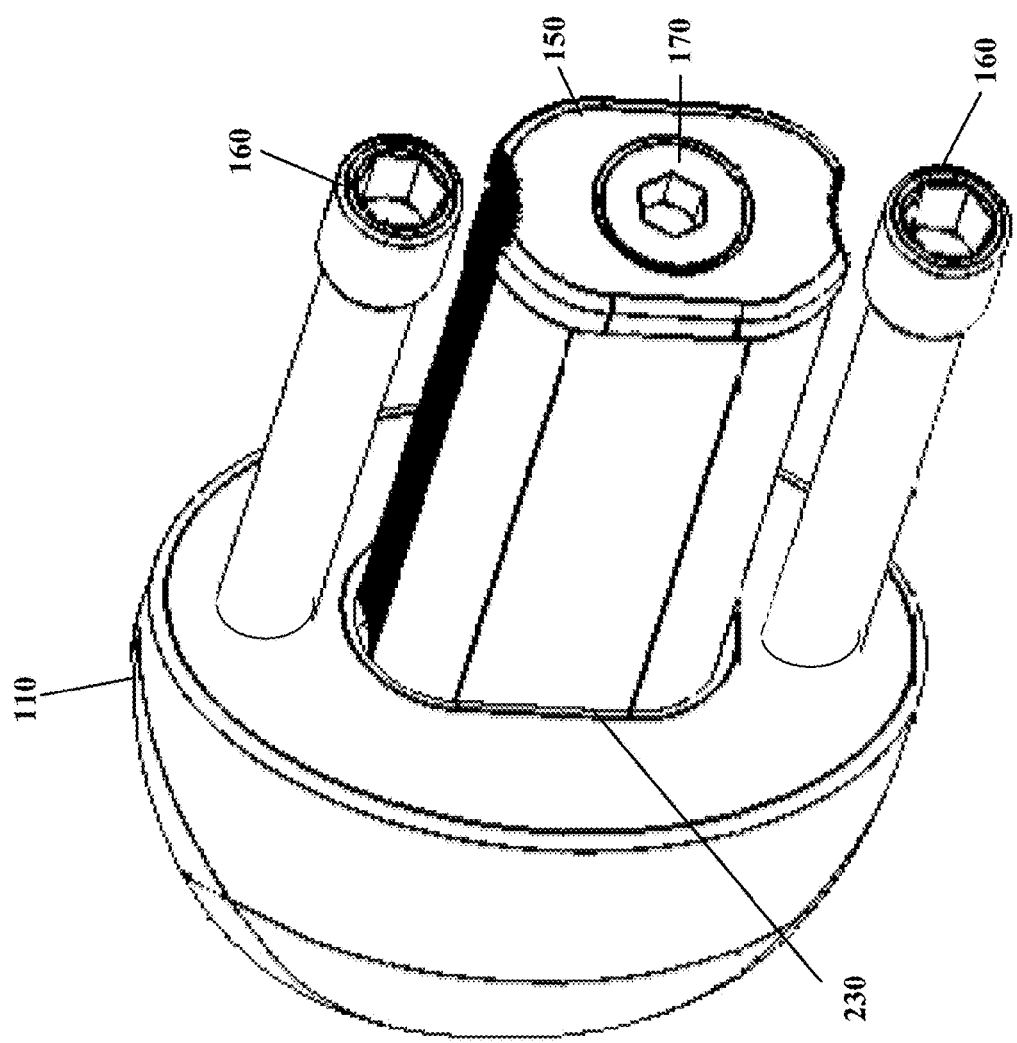
FIG. 9 is a medial view of the distal tip showing the coupled inferior and superior actuation screws and the locking insert with central bolt inserted, in accordance with an aspect of the present invention.

FIG. 9 shows a perspective view of the device 100 with the wings 130, the middle plate 120 and the proximal plate 140 removed. The superior and inferior actuation screws 160 are seen inserted into the corresponding securement holes 210 disposed in the inner planar surface of the distal tip member 110. Additionally, the locking insert 150 is shown positioned within the central depression 230 with the inner locking screw 170 threaded through the locking insert 150 and into the central hole 220 (not shown).

As seen in FIG. 3, the middle plate 120 may have two planar ends to facilitate the assembly of the device 100. The two ends will articulate with two pairs of wings when the device 100 is constructed. The outer shape of the middle plate 120 is oval or oblong to accommodate insertion between the two spinous processes, although other geometric shapes may also be used depending upon the clinical situation. The thickness of the middle plate 120 may vary depending upon the clinical situation and patient size. For example purposes, the middle plate thickness may range between 3-25 mm, with a preferred range of 3-15 mm. Superior and inferior screw holes extend through the entire thickness of the plate to accommodate the passage of the corresponding actuation screws 160. There is a centralized opening that is sized to permit the insertion of the locking insert 150 that then transacts the thickness of the middle plate 120 and extends into the proximately positioned distal tip member 110 for securement.

It should be understood that device 100 may include more than one intermediate spacer plates as shown. Although the device 100 is described as having a single middle plate 120, a plurality of such plates 120 may be used in the device construct depending upon a presented clinical situation.

Also shown in FIG. 3 is the proximal plate 140. The proximal plate 140 may be similarly constructed to the middle plate 120 in that it may have two planar ends to facilitate the assembly of the device 100. The inner end surface of the proximal plate 140 may articulate with one pair of wings when the device 100 is constructed. The outer end comprises the end aspect of the device 100. The outer shape of the proximal plate 140 is oval or oblong to accommodate placement between the two spinous processes, although other shapes may also be used depending upon the patient's anatomy. The thickness of the proximal plate 140 may vary depending upon the clinical situation and patient size. For example purposes, the proximal plate may have a thickness ranging from 2-25 mm, with a preferred thickness range of 2-10 mm. Superior and inferior screw holes extend through the entire thickness of the plate to accommodate the passage of the corresponding actuation screws 160. These holes also may include a counter bore or other like mechanism to accommodate the heads of the actuation screws 160 resulting in the heads being seated below the outer end surface so to eliminate any possible surrounding tissue complications. Proximal plate 140 also includes a centralized opening that is sized to permit the insertion of the locking insert 150 that then transacts the thickness through the proximal plate 140 and extends the entire length of the device 100 before seating into the proximately positioned distal tip member 110. The outer aspect of the centralized opening may include a counter bore or like configuration that allows the head or end portion of the locking insert to seat below the outer end surface when it has been fully inserted and secured.

As seen in FIGS. 1, 2 and 3, the device 100 typically includes four wings or fins 130 in its structure. The fins or wings 130 are movable relative to the proximal plate 140, the middle plate 120 and the distal tip member 110. Generally, one pair of wings 130, which are in opposing positions are secured between the proximal plate 140 and the middle plate 120. A second pair of similarly positioned wings 130 are secured between the middle plate 120 and the distal tip member 110. The wings 130 are shown shaped in an arcuate/tear drop configuration to facilitate expansion of the device in vivo. However, other shapes may be used depending upon the given clinical circumstances. Further, the wings 130 are shaped to maximize contact with the spinous processes without interfering with the surrounding soft tissue. Disposed on the outer tip aspect of each wing are fixation means 180, which for example purposes are shown in FIG. 1 as sharpened protrusions. It would be understood that various other means for fixation 180 may be used including spikes, teeth, pins and other heightened surface iterations. Also seen in FIG. 1 are holes 185. Holes 185 may be used to accommodate modular fixation means, including screws, pins and wires as well as being used to facilitate insertion of the device 100. Holes 185 may be numerous for each wing depending upon the given clinical situation. The range of the number of holes in each wing may be between 1-6, with a preferred range of between 1 and 4 holes. Wings 130 also include disposed on the curved inner edge surface, a series of raised teeth or like locking mechanism. The teeth are positioned on the inner edge surface of the wing to mechanically interact with a corresponding tooth pattern that is disposed on the top and bottom surface of the locking insert (see FIG. 9). For example purposes, the top and bottom surfaces of the locking insert 150 each have a corresponding concave trough that runs the length of the insert. Running parallel to and within the trough are a series of raised ribs which will interlock with the teeth of the wings 130. The wings 130 may be rotated through the arc of curvature of the inner edge surface and then secured when the appropriate orientation is achieved between the spinous processes. The range of rotation as measured from a fully retracted position may be from 0 to 270 degrees, although other degrees of angulation are contemplated. As noted above, each of the wings 130 may also have a plurality of through holes 185 that are used for bone fixation, alignment purposes and securement within the device assembly.

Figure 4:
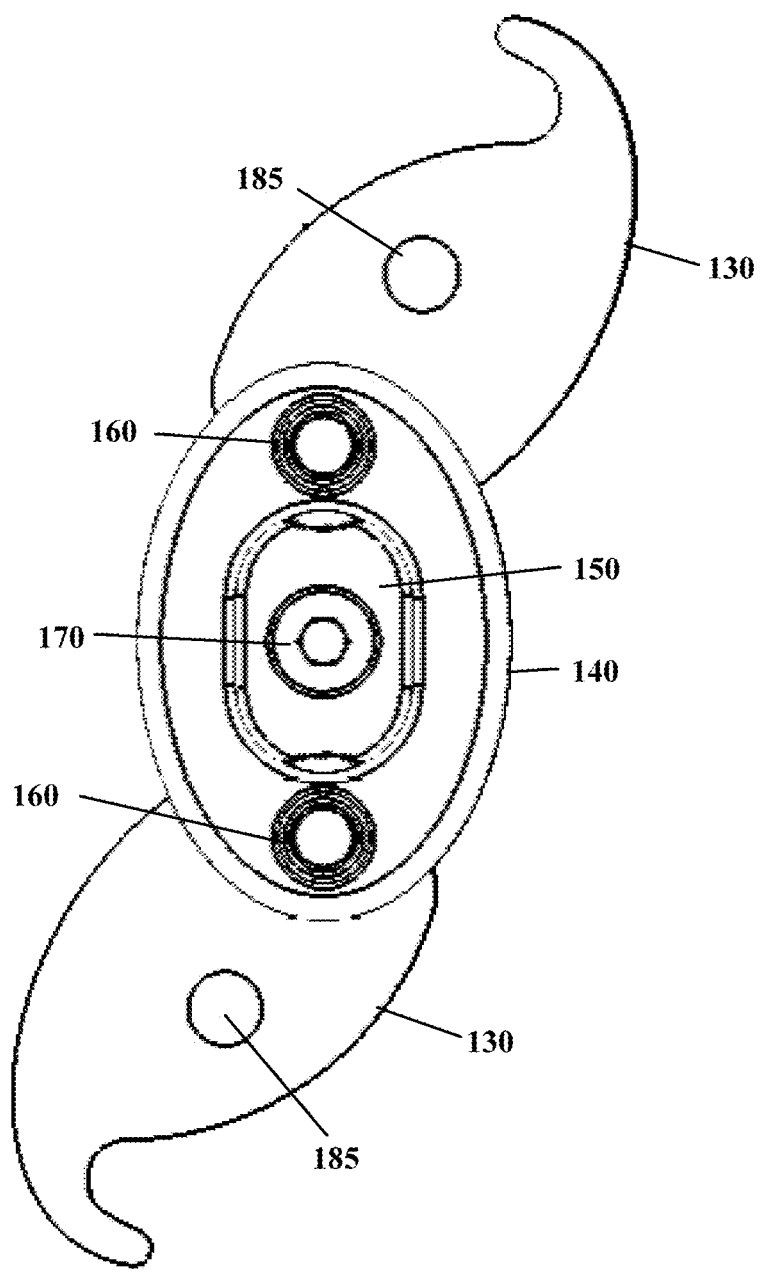
FIG. 4 is a lateral view of the interspinous process fusion device of FIG. 1 showing the wings angled at 210 degrees as determined from a fully retracted position, in accordance with an aspect of the present invention.
Figure 5:
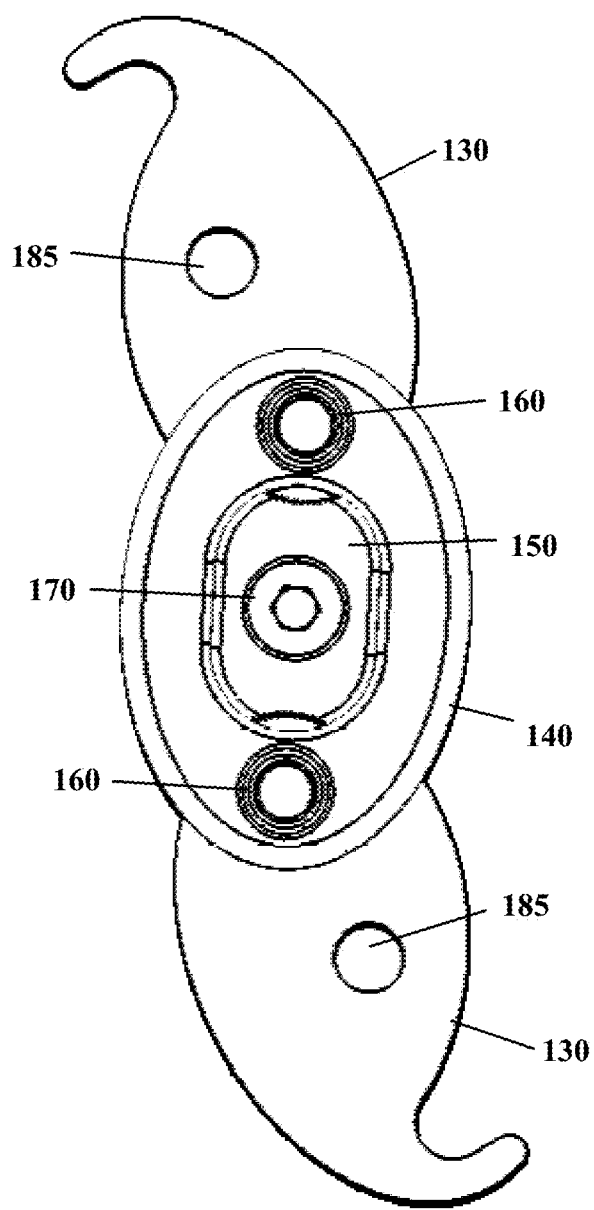
FIG. 5 is a lateral view of the interspinous process fusion device of FIG. 1 showing the wings angled at 150 degrees as determined from a fully retracted position, in accordance with an aspect of the present invention.

FIG. 4 shows both the superior and inferior wings 130 locked at 210 degrees from the fully retracted position. FIG. 5 shows the superior and inferior wings 130 locked at 150 degrees. Also shown in FIGS. 4 and 5 is the locking mechanism for the wings 130 that includes the concave ribbed trough of the locking insert 150 and the teethed portion of the inner edge surface of the wing. The superior and inferior wings are generally independent of each allowing the superior and inferior wings 130 to be angled to a different degree to address any anatomical issues or insertion difficulties. Wings 130 are moved by a rotation mechanism, which for example purposes may be a press-fit connection between actuation screws 160 and holes 200 in wings 130. Other rotation mechanisms are contemplated, including a gear configuration, moveable spline, and camming arrangement.

Figure 10:
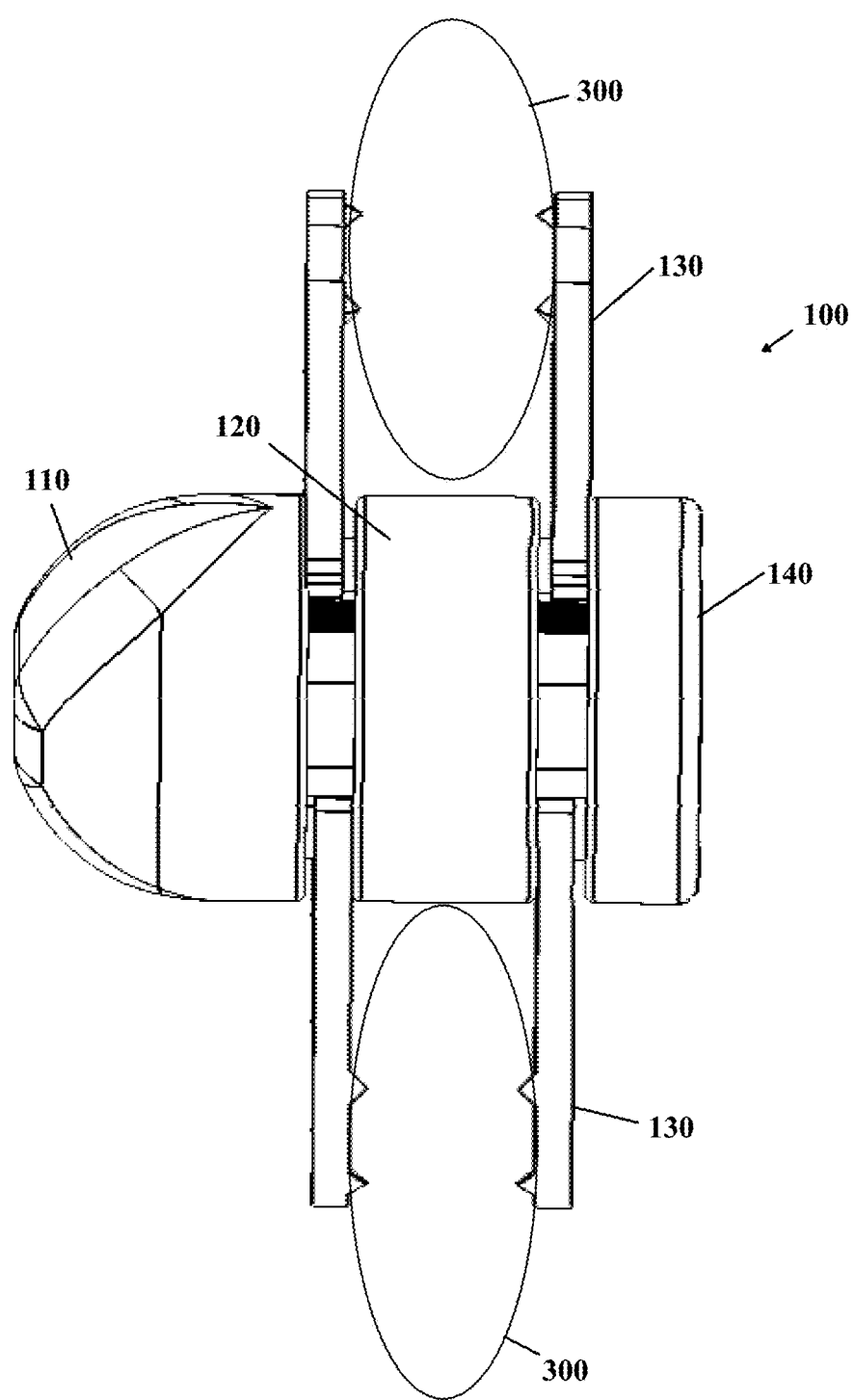
FIG. 10 is a posterior view of the interspinous process fusion device of FIG. 1, following implantation between two spinous processes, in accordance with an aspect of the present invention.
Figure 11:
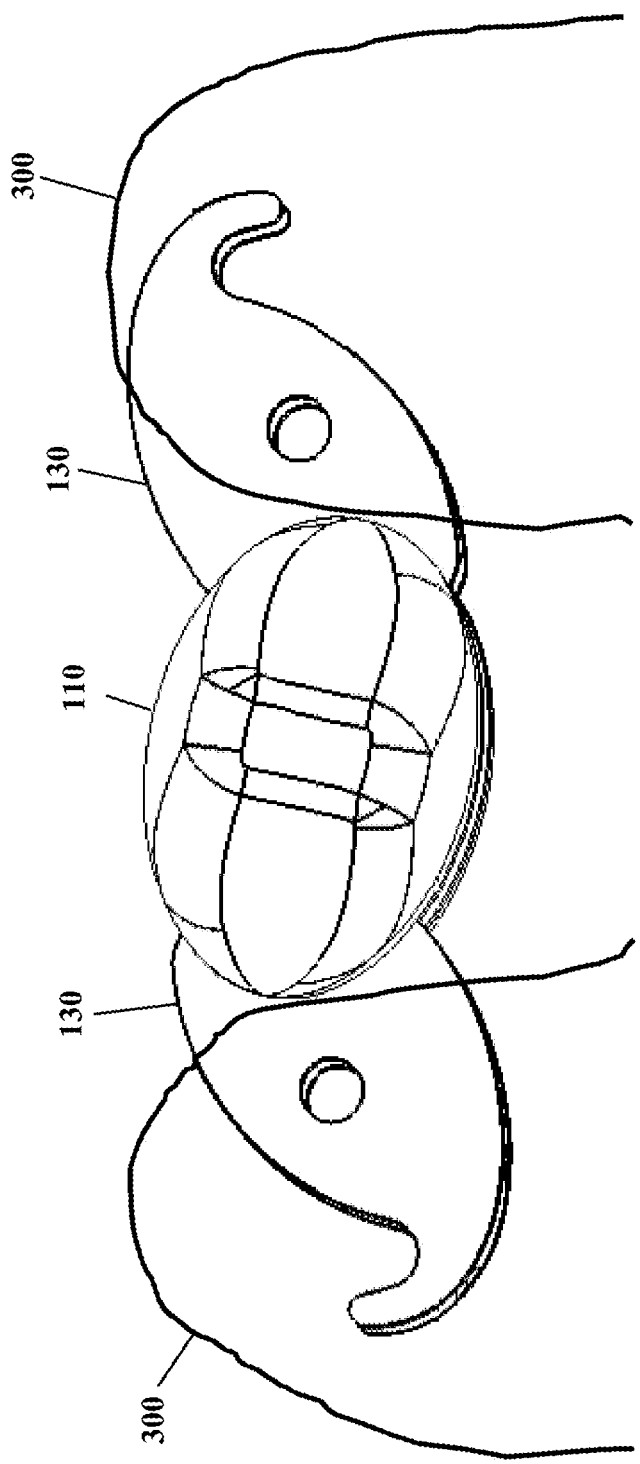
FIG. 11 is a lateral or side view of the interspinous process fusion device of FIG. 1, following implantation between two spinous processes, in accordance with an aspect of the present invention.

FIGS. 10 and 11 show the device 100 following implantation between two spinous processes 300. FIG. 10 is a posterior view of the implanted device 100 with the superior spinous process captured between the two superior wings 130 and secured by the means of fixation which contact and grip the bone surface. With the inferior spinous processes, this bone protuberance is also trapped between the two inferior parallel oriented wings 130. FIG. 11 is a lateral view showing the device 100 in place following implantation within the spine. Wings 130 are in contact with both lateral surfaces of the two adjacent spinous processes. The device 100 is also seen to have an outer configuration such that the external profile of the device 100 does not extend beyond the apex or tip of either of the two processes. Because the device has a low profile, post operative soft tissue complications are decreased or eliminated.

Figure 6:
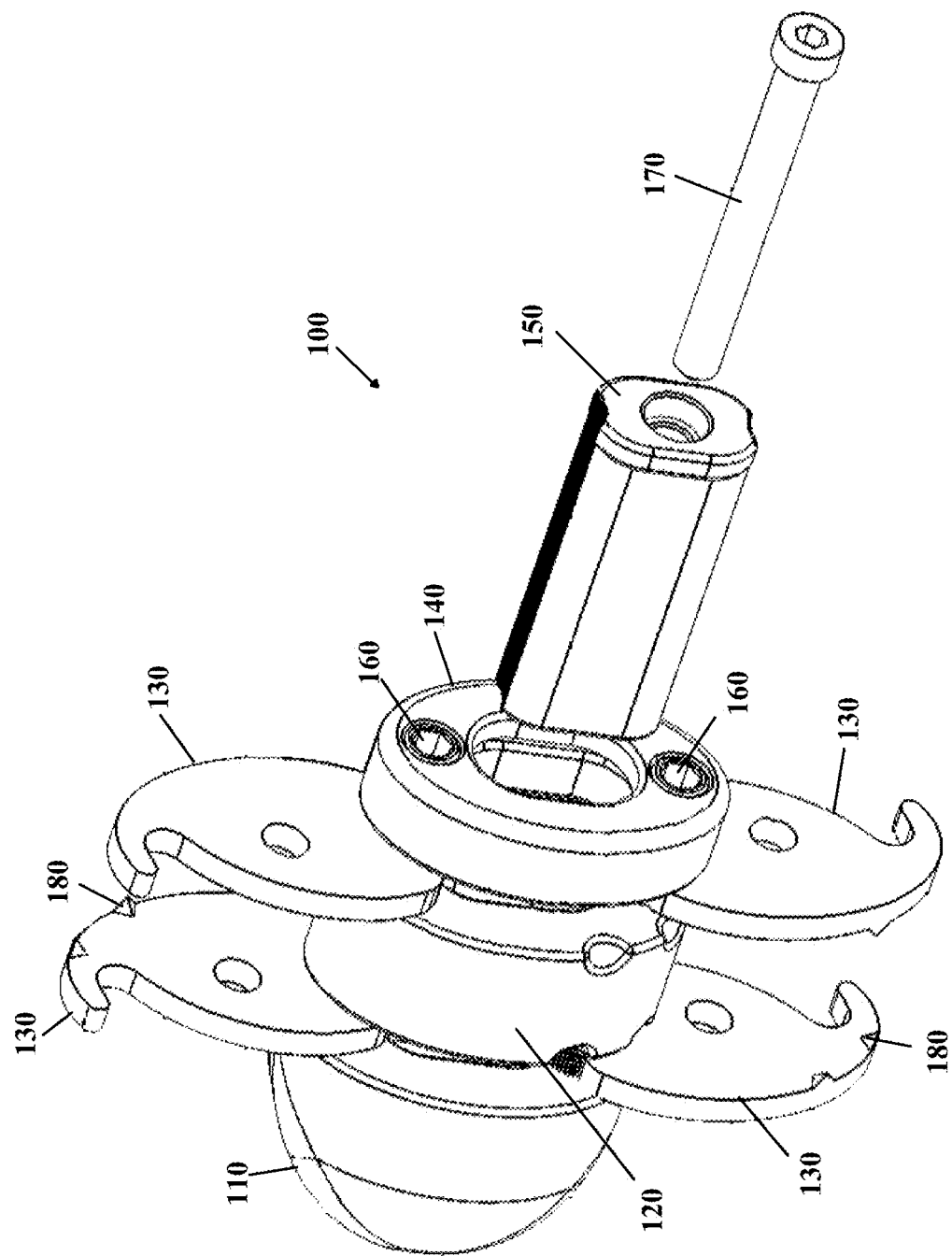
FIG. 6 is a posterior, lateral perspective view of the interspinous process fusion device of FIG. 1 showing the locking insert and center bolt prior to insertion into the device assembly, in accordance with an aspect of the present invention.

FIG. 6 shows the locking insert 150 prior to insertion into the centralized opening of the device 100. For example purposes, the locking insert 150 may be generally rectangular in shape with an overall length that mirrors the length of the device when assembled. It is contemplated that other cross-sectioned geometries may also be used in the construction of locking insert 150. A central through hole extends the entire length and is sized to allow for the insertion of the inner locking screw 170. The entry opening of the centralized hole may include a counter bore or like configuration to accommodate the head of the inner locking screw 170 and avoid potential soft tissue impingement issues. As discussed above, for example purposes, the top and bottom surfaces of the locking insert 150 each have a concave trough that runs the length of the insert. Running parallel to and within the trough are a series of raised ribs or projections which will interlock with corresponding teeth of the wings 130 to secure the wings position and form a locking mechanism. It is contemplated that other mechanical configurations may be used to accomplish the locking of the wings relative to the locking insert, including possible frictional engagement between the wings 130, and plates 120, 140 and distal tip member 140.

FIG. 3 also shows inner locking screw 170 and superior and inferior actuation screws 160. The inner locking screw 170 is configured to pass through the central portion of the locking insert 150 and then couple to the distal tip member 110. The inner locking screw 170 functions to hold all of the components together when the assembly is constructed in a skewer like fashion. It is contemplated that other mechanical fixation devices may be used for this function, including locking pins or rods. For example, a compression o-ring may be used to lock the inner locking screw 170 to the device 100 to prevent backout. The superior and inferior actuation screws 160 are positioned above and below the locking insert 150 and may also apply a compressive load on the construct to lock the wings 130 in position. The actuation screws 160 extend through all of the elements of the device, including the wings and couple to the distal tip member 110 such that when tightened the actuation screws 160 may apply a compressive load across the entire span of the device 100 to secure all of the elements in position. It should be understood that other alternative modes of fixation may be employed including, but not limited to locking pins and rods.

Figure 7:
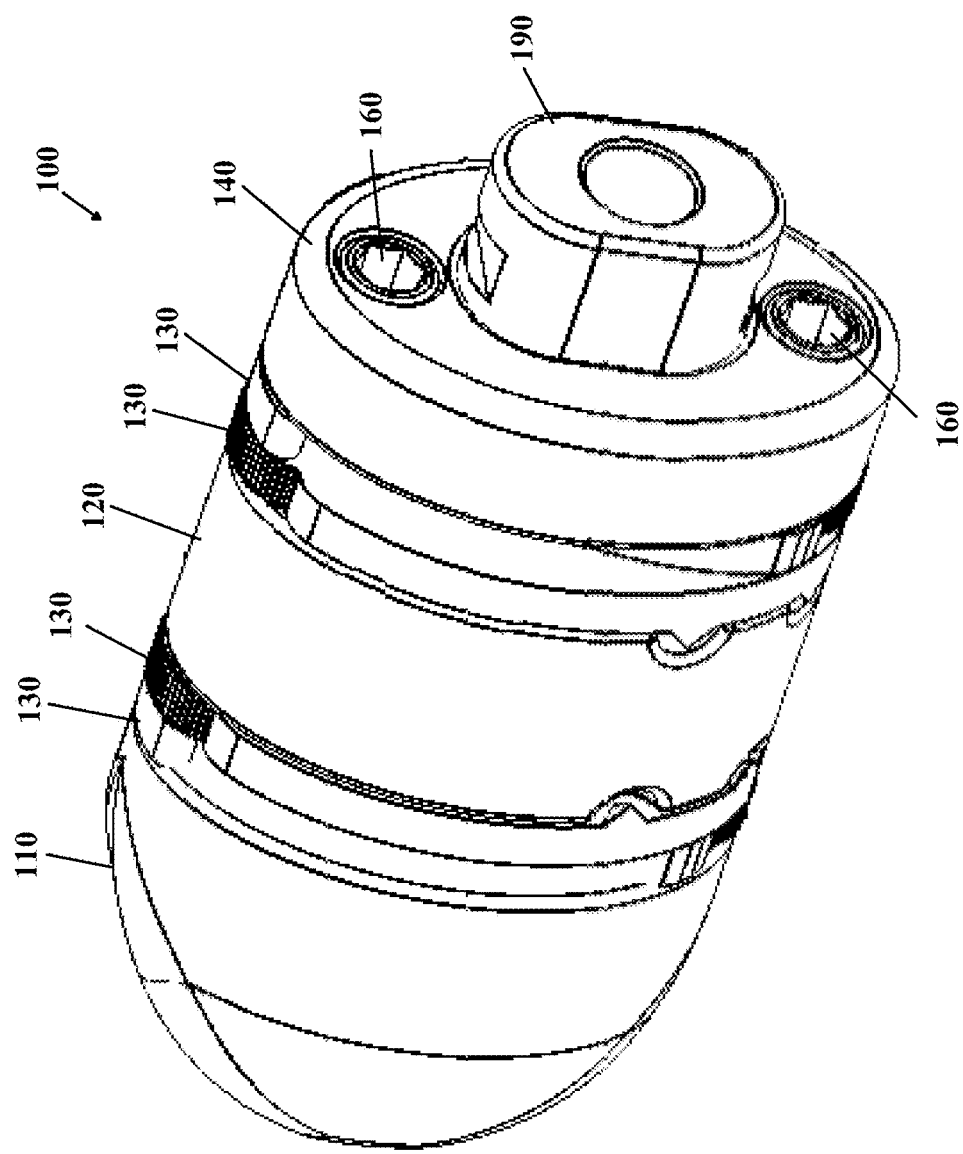
FIG. 7 is a posterior, lateral perspective view of the interspinous process fusion device of FIG. 1 showing the device in a collapsed position prior to insertion between two spinous processes, in accordance with an aspect of the present invention.

As discussed above, the device operates in two states, expanded as shown in FIG. 1 and contracted as seen in FIG. 7. The surgeon utilizes the device in its contracted state when it is being implanted during a MIS procedure. The device 100 in its contracted position is fully assembled and includes the distal tip member 110, the middle plate 120, the proximal plate 140 with one pair of wings 130 sandwiched between the distal tip member 110 and the middle plate 120 and the second pair of wings 130 between the middle plate 120 and the proximal plate 140. Compressing the assembly is a temporary insertion insert 190 that has a configured end that is coupled to an insertion tool (not shown). In the collapsed state, the device 100 has a uniform or cylindrical like exterior profile that may be described as being bullet shaped. The wings 130 have been internally rotated to the extent that the wings outer edges are fully within the outer boundaries/surfaces of the middle and proximal plates, hence producing a uniform outside profile to facilitate implantation.

Figure 12:
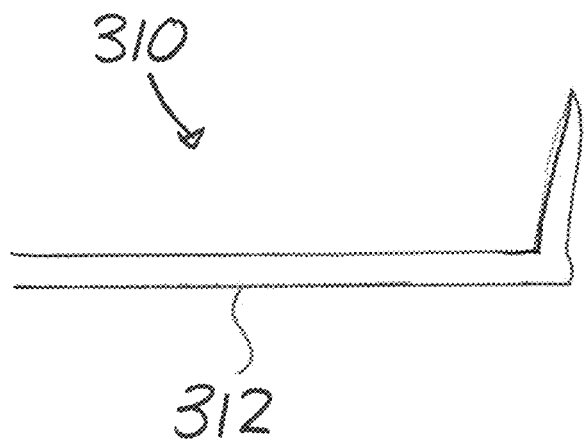
FIG. 12 is a side view of a cutting tool to open the space for the expansion of the wings, in accordance with an aspect of the present invention.
Figure 13:
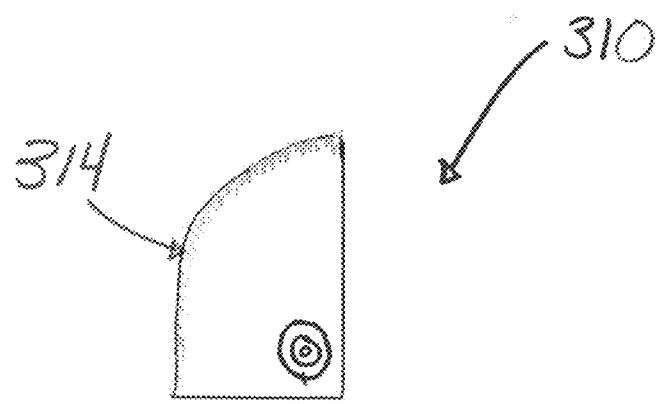
FIG. 13 is a front view of the cutting tool of FIG. 12, in accordance with an aspect of the present invention.

Once the device 100 is implanted between the superior and inferior spinous processes the insertion insert 190 is removed, the wings 130 are rotated and expanded out and the locking insert is slid into the central opening to secure the position of the wings 130. The inner locking screw 160 is tightened to pressingly secure the assembly and the fix via the locking mechanism (corresponding teeth/rib arrangement) the wings angled position. In order to open the space for the wings 130 prior to insertion of the device 100, a cutting tool 310 may be inserted into the subcutaneous pathway to cut any soft tissue in the path of the wings 130. As illustrated in FIGS. 12 and 13, the cutting tool 310 may have a handle 312 and a blade 314.

The method of assembling the device 100 may include the steps of choosing a locking insert 150 sliding the proximal plate 140 over the insert until it abuts the proximal end. A next step may be to insert the superior and inferior actuation screws 160 into the proximal plate 140. The method may then include the step of sliding a first wing 130 onto the superior actuation screw 160 and a first wing 130 onto the inferior actuation screw 160 and sliding both wings 130 until they are adjacent to the proximal plate 140. The method may also include the step of sliding the middle plate along the locking insert 150 and the two actuation screws 160 until the middle plate 120 is adjacent to the previously positioned pair of wings 130. The method may also include the step of sliding a second wing 130 onto the superior actuation screw 160 and a second wing 130 onto the inferior actuation screw 160 and sliding both wings 130 until they are adjacent to the middle plate 120. The method may include the step of selecting a certain sized distal tip member 110 and sliding this onto the ends of the locking insert 150 and the actuation screws 160. The actuation screws 160 may then be rotated to adjust the angulation of the wings 130 and thereby thread into the distal tip member 110. The method may also have the step of inserting the inner locking screw 170 into the centralized hole of the locking insert 150 and then threading the end into corresponding threaded hole disposed within the distal tip member 110 to compress and secure the assembly into one construct.

Several biocompatible materials may be used to fabricate the elements, including a myriad of metals, polymers, ceramics and composites. Examples of these include PEEK, titanium and stainless steel.

The example minimally invasive surgical method for using the device 100 includes the steps of inserting the device subcutaneously between the cephalad or top spinous process and the caudal or bottom spinous process while the device is in its collapsed state with the wings 130 retracted. This subcutaneous pathway may be created through an independent incision, or through the DLIF, TLIF, or unilateral decompression of stenosis incision (1½ cm off midline). The method may also include the step of positioning the device between the two spinous processes. The method may further include the step of deploying the wings 130 in both the cephalad and caudal direction and on both sides of the spinous processes. The method may further include the step of compressing the device with the inner locking screw to pressingly engage from a lateral to medial direction the wings 130 with the two sides of the spinous processes. Sharp pins in the wings 130 hold the device in place. Once the device is secured, the tightening instrument is removed and the incision is closed.

Figure 14:
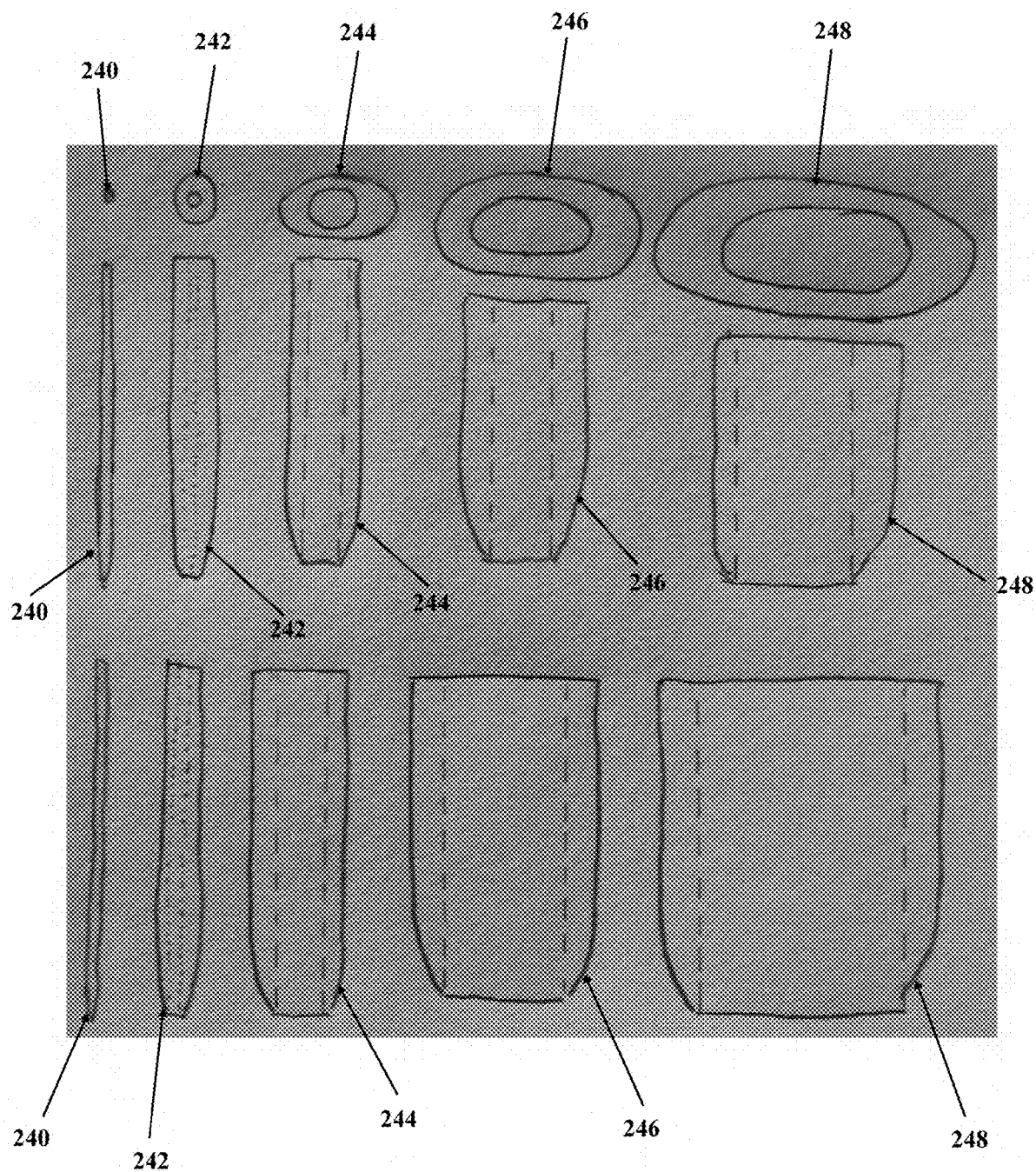
FIG. 14 is top and side views of a set of dilators, in accordance with an aspect of the present invention.

More specifically, the surgical method for using the device 100 includes the steps of creating an incision at the site where the implant will be inserted. Preparing the site for insertion of the device 100, by for example, chiseling to cut or trim the spinous processes to accept the device 100. Then a series of a plurality of dilators of increasing size may be inserted to expand the space between the spinous processes. For example, a first circular dilator 240 could be inserted into an incision in the patient. Then a second circular dilator 242 with a larger diameter could be inserted over the first dilator 240 to increase the size of the opening. It is also contemplated that only one circular dilator could be used. Alternatively, a plurality of circular dilators could be used. Next a third dilator 244 with a slightly oval shape could then be inserted over the second dilator 242 to increase the size of the opening. A fourth dilator 246 with a larger oval shape than the third dilator 244 could then be inserted next over the third dilator 244, wherein the first, second, and third dilators 240, 242, 244, respectively, are in a center opening within the fourth dilator 244. A plurality of additional dilators could then be inserted over the prior dilator until a dilator having a size that matches the size of the device 100 has been used. As depicted the additional dilators may include only one dilator, such as fifth dilator 248. Alternatively, the additional dilators may include multiple additional dilators of increasing size. The circular dilators may have a diameter ranging from approximately 4 mm to 8 mm and a length ranging from approximately 20 mm to 50 mm. The oval dilators will have sizes ranging from a height of approximately 5 to 25 mm, with preferred sizes ranging from 7 to 22 mm, a width of approximately 4 to 16 mm, with a preferred width size of 5 to 15 mm, and a length range of approximately 20 mm to 55 mm. An example of a set of dilators is shown in FIG. 14.

Once the pathway has been enlarged to the size of the device 100, all of the dilators may be removed and trials of the device 100 may be inserted through the pathway to a space between the two spinous processes 300 to determine the desired size of the device 100. The trials will have exterior sizes that are equivalent to the sizes of the device 100 and may contain a handle for ease of insertion and removal from the patient. For example, the trials may have a height of approximately 8 to 16 mm, a width of approximately 4 to 8 mm, and a length of approximately 20 mm. When the surgeon determines which trial best fits between the two spinous processes 300, the surgeon will select the equivalent device 100 and insert it into the patient. After the device 100 is inserted and positioned between the two spinous processes 300, the plurality of movable wings 130 may be expanded to engage the spinous processes 300. After the plurality of movable wings 130 are expanded the device 100 may be locked in the desired position and the patient may be closed up.

Although the example embodiments have been depicted and described in detail herein, it will be apparent to those skilled in the relevant art that various modifications, additions and substitutions can be made without departing from its essence and therefore these are to be considered to be within the scope of the following claims.

What is claimed is:

1. A surgical method for maintaining a space between two spinous processes in a spine of a patient, comprising:
    obtaining a medical device comprising: a distal tip member, a middle plate, a proximal plate, an elongate member having a first end, a second end, and a longitudinal axis extending between the first end and the second end, and a plurality of movable wings, wherein the distal tip member is connected to the first end of the elongate member and the proximal plate is connected to the second end of the elongate member with the middle plate and plurality of wings being positioned intermediate the distal tip member and the proximal plate along the longitudinal axis of the elongate member;
    inserting the medical device through an opening in the skin of the patient;
    positioning the medical device between a top spinous process and a bottom spinous process;
    moving the plurality of wings to pressingly engage the top spinous process and the bottom spinous process to maintain the space therebetween; and
    inserting an inner locking screw into a hole in the elongate member to secure the medical device to the top spinous process and the bottom spinous process.

2. The surgical method of claim 1, further comprising:
    inserting a first dilator through the opening in the skin of the patient prior to inserting the medical device, wherein the first dilator is circular.

3. The surgical method of claim 2, further comprising:
    inserting a second dilator through the opening in the skin of the patient and over the first dilator prior to inserting the medical device, wherein the second dilator is slightly oval.

4. The surgical method of claim 3, further comprising:
    inserting a third dilator through the opening in the skin of the patient and over the second dilator prior to inserting the medical device, wherein the third dilator is oval.

5. The surgical method of claim 4, further comprising:
    inserting a plurality of fourth dilators through the opening in the skin of the patient and over at least one of the third dilator and the previous fourth dilator, wherein each fourth dilator of the plurality of fourth dilators is slightly larger than the previous fourth dilator, and wherein the plurality of fourth dilators are ovals of increasing size.

6. The surgical method of claim 5, wherein the largest of the plurality of dilators is sized to correspond with an exterior shape of the medical device for insertion into the patient.

7. The surgical method of claim 5, wherein the plurality of dilators are sized to include a height of approximately 5 to 25 mm, with a preferred height ranging from 7 to 22 mm, a width of approximately 4 to 16 mm, with a preferred width size of 5 to 15 mm, and a length range of approximately 20 mm to 55 mm.

8. The surgical method of claim 1, further comprising:
    closing the opening in the skin of the patient.

9. The surgical method of claim 1, wherein the plurality of movable wings comprises a first pair of movable wings and a second pair of movable wings.

10. The surgical method of claim 9, wherein the first pair of movable wings comprises a first fin and a second fin and the second pair of movable wings comprises a third fin and a fourth fin.

11. The surgical method of claim 10, wherein each of the first fin, the second fin, the third fin and the fourth fin further comprise a lateral side and a medial side.

12. The surgical method of claim 11, wherein the medial side is planar, and wherein the medial side of the first fin and the third fin contact the top spinous process and the medial side of the second fin and the fourth fin contact the bottom spinous process to maintain the space therebetween.

13. The surgical method of claim 12, wherein a fixation means extends from each of the medial sides of the first fin, the second fin, the third fin and the fourth fin to secure the medical device to at least one of the top spinous process and the bottom spinous process.

14. The surgical method of claim 13, wherein the fixation means comprises at least one of spikes, teeth and pins, wherein the ends of the fixation means are configured to engage an outer bone surface of at least one of the top spinous process and the bottom spinous process.

15. The surgical method of claim 11, wherein each of the first fin, the second fin, the third fin and the fourth fin further comprise at least one opening, wherein the at least one opening extends from the lateral side to the medial side of each of the fins.

16. The surgical method of claim 15, wherein the at least one opening is configured to accommodate at least one of a screw, pin and wire to facilitate securement of the medical device to at least one of the top spinous process and the bottom spinous process.

17. A surgical method for maintaining a space between two spinous processes in a spine of a patient, comprising:
    obtaining a medical device comprising: a distal tip member, a middle plate, a proximal plate, an elongate member having a first end, a second end, and a longitudinal axis extending between the first end and the second end, and a plurality of movable wings, wherein the distal tip member is connected to the first end of the elongate member and the proximal plate is connected to the second end of the elongate member with the middle plate being positioned intermediate the distal tip member and the proximal plate along the longitudinal axis of the elongate member, wherein the plurality of movable wings are offset along the longitudinal axis, wherein the plurality of movable wings comprises at least a first pair of movable wings with a first wing and a second wing and a second pair of movable wings with a third wing and a fourth wing, and wherein in a first position the first wing is positioned between the proximal plate and the second wing, the second wing is positioned between the first wing and the middle plate, the third wing is positioned between the middle plate and the fourth wing, and the fourth wing is positioned between the third wing and the distal tip member;

inserting the medical device through an opening in the skin of the patient;

positioning the medical device between a top spinous process and a bottom spinous process; and rotating the plurality of wings to position the plurality of wings to pressingly engage the top spinous process and the bottom spinous process to maintain the space therebetween.

18. The surgical method of claim 17, wherein rotating the plurality of wings comprises deploying each of the plurality of wings from the first position to a second position, wherein a first set of the plurality of wings rotates each wing of the first set from the first position where a first end is superior to a central opening to the second position where the first end is inferior to the central opening, and wherein a second set of the plurality of wings rotates each wing of the second set from the first position where a first end is inferior to the central opening to the second position where the first end is superior to the central opening.

19. The surgical method of claim 17, wherein the medical device further comprises: a temporary insert positioned within a central opening of at least the proximal plate; and wherein the method further comprises:

removing the temporary insert from the medical device before rotating the plurality of wings.

* * * * *